United States Patent [19]

Barrett

[11] Patent Number: 5,085,214
[45] Date of Patent: Feb. 4, 1992

[54] INFLATABLE CUSHION FOR SUPPORTING AN EXTREMITY

[75] Inventor: Patrick J. Barrett, St. Louis, Mo.

[73] Assignee: Twenty-First Century Products, Incorporated, St. Louis, Mo.

[21] Appl. No.: 600,011

[22] Filed: Oct. 18, 1990

[51] Int. Cl.⁵ .......................... A61G 15/00; A61F 5/37
[52] U.S. Cl. ................................... 128/845; 128/882; 128/DIG. 20
[58] Field of Search ............... 128/DIG. 20, 87 R, 85, 128/89 R, 882, 878, 879, 165, 160, 157, 845

[56] References Cited

U.S. PATENT DOCUMENTS

| | | | |
|---|---|---|---|
| 3,193,984 | 7/1965 | Schubert | 128/DIG. 20 |
| 3,279,459 | 10/1966 | Schenker | 128/DIG. 20 |
| 3,462,775 | 8/1969 | Markwitz | 128/DIG. 20 |
| 3,717,145 | 2/1973 | Berndt | 128/DIG. 20 |
| 4,106,499 | 8/1978 | Ueda | 128/DIG. 20 |
| 4,300,759 | 11/1981 | Caplan | 128/DIG. 20 |
| 4,597,384 | 7/1986 | Whitney | 128/DIG. 20 |
| 4,620,530 | 11/1986 | Lanier | 128/75 |
| 4,628,945 | 12/1986 | Johnson, Jr. | 128/DIG. 20 |
| 4,739,752 | 4/1988 | Cohen | 128/DIG. 20 |
| 4,938,208 | 7/1990 | Dye | 128/DIG. 20 |

Primary Examiner—Robert A. Hafer
Assistant Examiner—Michael Brown
Attorney, Agent, or Firm—Senniger, Powers, Leavitt & Roedel

[57] ABSTRACT

An inflatable cushion for elevation of an extremity with respect to a surface supporting the cushion including an inflatable bladder having first and second opposite ends and inner and outer faces. The bladder is equipped with an air inlet for admitting air into the bladder for inflation of the bladder which includes a valve to selectively seal and unseal the air inlet. The first and second ends of the bladder may be fastened together by cooperating fasteners attached to each end. A lining made of a soft absorbent material substantially covers the inner face of the bladder. The bladder may be inflated, wrapped around the extremity and secured by the fasteners so that the bladder completely encircles the extremity. As applied to the extremity, the inner face of the bladder faces inwardly with the lining disposed between the bladder and the extremity and engaging the extremity. An area of the inner face underlying the extremity resiliently deforms under the weight of the extremity such that the weight of the extremity is supported substantially uniformly over the underlying area. The outer face of the bladder faces outwardly with a portion of the outer face engaging the surface.

6 Claims, 2 Drawing Sheets

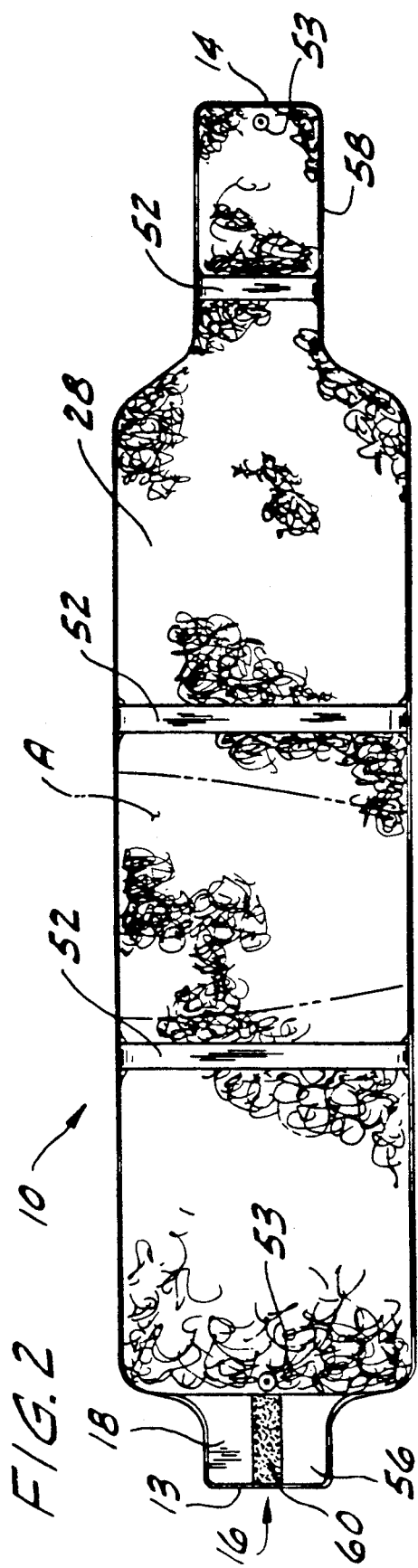
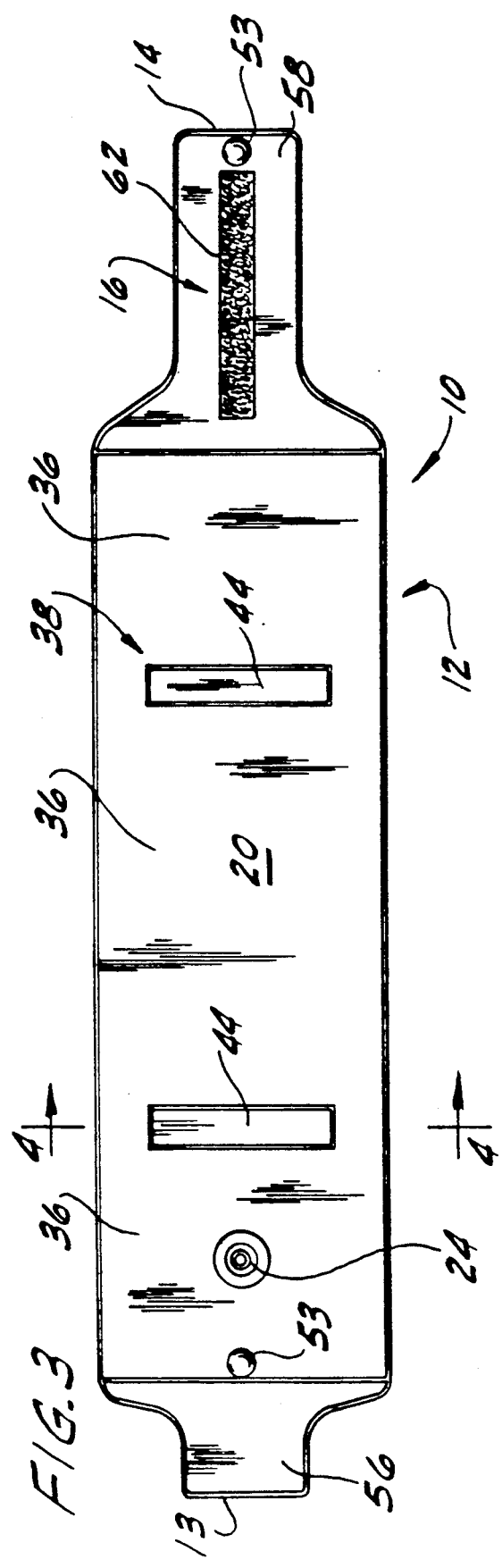

INFLATABLE CUSHION FOR SUPPORTING AN EXTREMITY

BACKGROUND OF THE INVENTION

This invention relates generally to medical devices for supporting extremities and more specifically to an inflatable cushion for elevated support of an extremity.

Elevation of an extremity has several well known therapeutic applications, including reducing swelling by encouraging gravitational flow of blood out of the extremity. Moreover, supporting the extremity away from other surfaces, such as a bed mattress, prevents the occurrence of bed sores and promotes the healing of damaged tissue. In the past, elevation of the extremities has been accomplished primarily through the use of pillows or cushions, used individually or stacked to achieve an appropriate elevation. Air mattresses, padded boots and padded socks have been used to cushion the extremity at a pressure point (e.g., the back of the heel or the elbow) to prevent the occurrence of bed sores.

Bed sores are a common problem among patients, and particularly older patients, who are confined to bed with a limited ability to move. Pillows, padded boots and padded socks are relatively soft and deformable, but they lack resiliency so that the weight of the extremity tends to be supported over a small area of the extremity, causing a pressure point. Although air mattresses are resilient, a disproportionately high amount of its weight is supported over a small area of the extremity such as the heel or elbow. Other devices, such as small inflatable annular rings can support the heel or elbow away from the bed, but these devices still support the weight of the extremity over such a small area that circulation around the heel or elbow often is cut off. The existence of the pressure point causes pain in the extremity because of the concentration of force on a small surface area of the extremity. The presence of a pressure point leads to break down of the skin tissue causing a bed sore, and the presence of an open wound raises the potential for infection.

If the extremity can be moved the pressure point may be changed, but the pain will only recur in time. Moreover, movement of the extremity can cause the extremity to fall off the pillows or cause a stack of pillows to fall over. This is particularly a problem when a patient must have his extremity elevated for an extended period of time and changes position in bed periodically to maintain comfort. In addition, the patient's skin may have an allergic reaction to the material of the pillow, padded boot or padded sock.

SUMMARY OF THE INVENTION

Among the several objects of the present invention may be noted the provision of an inflatable cushion for elevation of an extremity which supports the extremity comfortably, preventing the occurrence of pressure points; the provision of such a cushion which maintains elevation despite movement of the extremity; the provision of such an inflatable cushion which prevents breakdown of skin contacting the cushion; the provision of such an inflatable cushion which reduces the chance of an allergic reaction of the skin contacting the cushion; the provision of such an inflatable cushion which inhibits growth of infectious bacteria adjacent the skin; the provision of such an inflatable cushion which is washable and requires little space to store when not in use; the provision of a cushion which is lightweight; and the provision of such an inflatable cushion which is inexpensive and thus readily afforded by individuals.

Generally, an inflatable cushion constructed according to the principles of the present invention comprises, an inflatable bladder having first and second opposite ends and inner and outer faces. The first and second ends of the bladder may be releasably fastened together by fastening means. Inlet means provided for admitting air into the bladder for inflation of the bladder may be selectively sealed and unsealed by selective sealing means. Lining means made of a soft absorbent material substantially covers the inner face of the bladder. The bladder is adapted to be inflated, wrapped around the extremity and secured by the fastening means such that the bladder completely encircles the extremity. When applied to the extremity, the inner face of the bladder faces inwardly with the lining means disposed between the bladder and the extremity and engaging the extremity. An area of the inner face underlying the extremity resiliently deforms under the weight of the extremity such that the weight of the extremity is supported substantially uniformly over the underlying area of the inner face. The outer face of the bladder faces outwardly with a portion of the outer face engaging the surface.

Other objects and features of the present invention will be in part apparent and in part pointed out hereinafter.

BRIEF DESCRIPTION OF THE DRAWINGS

FIG. 2 is a plan view of an inner face of the cushion;

FIG. 3 is a plan view of the outer face of the cushion; and

Corresponding reference characters indicate corresponding parts throughout the several views of the drawings.

DETAILED DESCRIPTION OF THE PREFERRED EMBODIMENT

Figure 1:
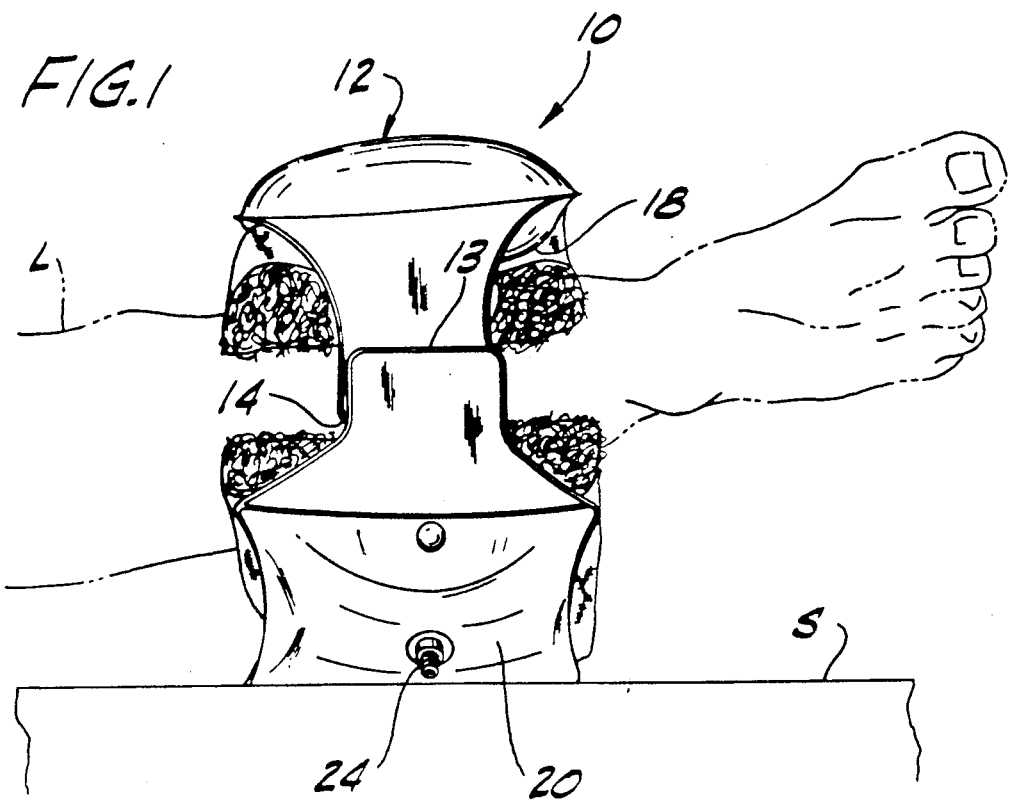
FIG. 1 is an elevation of the inflatable cushion of the present invention as applied to a leg.

Referring to the drawings, an inflatable cushion of the present invention, indicated in its entirety by the numeral 10, is shown to include an elongate bladder 12 made of a flexible, air impermeable material (e.g., vinyl) and having a first end 13 and a second end 14 longitudinally opposite the first. Fastening means indicated generally at 16 is provided for releasably fastening the first and second ends 13, 14 of the bladder together. The bladder 12 further includes an inner face 18 and an outer face 20, the directions "inner" and "outer" describing the relationship of the faces when the cushion 10 is applied to an extremity as described below. The bladder 12 of the preferred embodiment is approximately 32 inches long and 7 inches wide, although the precise dimensions are not critical to the invention. Inlet means, including a tube 24 projecting outwardly from an opening the bladder 12, is provided for admitting air into the bladder for inflating the bladder. A valve (broadly "selective sealing means") incorporated in the tube 24 allows the inlet means to be selectively sealed, by pushing the tube inwardly toward the bladder 12, or unsealed by pulling the tube outwardly from the bladder. The valve is a push-pull valve, model no. 320-AC, sold by Halkey-Roberts, Inc. of St. Petersburg, Fla. A lining 28 (broadly "lining means") comprising an elongate piece of lambs wool or similar soft absorbent material substantially covers the inner face 18 of the bladder.

The cushion 10 is particularly designed and constructed for elevation of an extremity (e.g., a leg L as shown in FIG. 1) with respect to a surface S, such as a mattress, supporting the cushion. In the following, the cushion 10 of the present invention will be described as applied to the leg L. However, it is to be understood that the cushion 10 may be used to elevate any of the extremities. The bladder 12 may be inflated by pulling out the tube 24 to open the valve and forcing air into the bladder through the tube. Although the bladder 12 is preferably filled with air, it is to be understood that the inflation of the bladder 12 as described herein may include filling the bladder with any gas or with a liquid. The bladder 12 may then be wrapped around the leg L and its first and second ends 13, 14 secured together by the fastening means 16 so that the bladder 12 completely encircles the leg. As applied to the leg, the inner face 18 of the bladder 12 faces inwardly toward the leg with the lining 28 being disposed between the inner face and the leg and engaging the leg. An area A of the inner face 18 underlying the lining 28 and the leg L and supporting the leg is illustrated by an outline in phantom in FIG. 2. This area A of the inner face 18, supported by the air inflating the bladder 12, resiliently deforms under the weight of the leg such that the weight of the leg is supported substantially uniformly over the area A and no pressure points are present. The cushion 10 is applied to the fleshy portion of the leg generally at the calf which lacks any bony protuberances. By supporting the leg away from the normal pressure point (i.e., the heel) at a fleshy portion of the leg, the weight of the leg is applied uniformly over the area A of contact with the cushion.

The outer face 20 of the bladder 12 faces outwardly and a portion of the outer face engages the surface S on which the leg L is supported. Because the bladder 12 completely encircles the leg, the cushion 10 will continually support the leg in its elevated position with respect to the surface S despite movement of the leg. This is of particular advantage to a person who must lie down for extended periods of time with his leg elevated. In order to remain comfortable, the person must move his body to shift the portions of this body which contact the supporting surface (e.g, bed mattress) which will inevitably result in movement of the elevated leg L. The cushion 10 of the present invention allows movement of the leg to occur while maintaining the appropriate elevation of the leg. Encirclement of the leg L by the cushion 10 also provides a barrier preventing inadvertent contact of the leg L with the other leg. This is particularly important when the leg is healing from tissue damage (e.g., burns), to prevent pain and/or further damage to the tissue.

Figure 4:
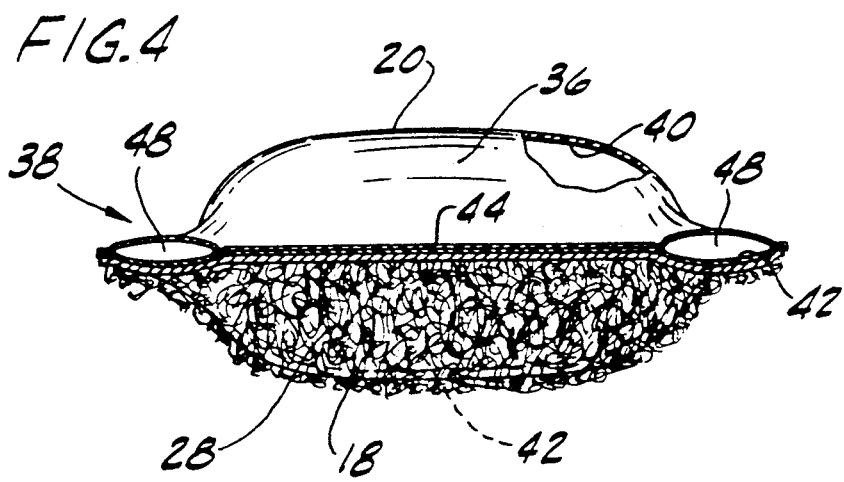
FIG. 4 is a section taken in the plane including line 4—4 of FIG. 3.

To facilitate bending of the inflated bladder 12 necessary for wrapping the cushion 10 around the leg L, the bladder has been constructed with a plurality of inflatable sections 36 separated by regions indicated generally at 38 which retain their flexibility despite inflation of the bladder (FIG. 3). As shown in FIG. 4, the bladder 12 further includes internal opposing walls designated 40 and 42 respectively, which are connected together at their edge margins to define the airtight interior of the bladder. To form the flexible regions 38 of the bladder, portions of the walls 40, 42 directly opposite each other are joined together in two places along the length of the bladder 12 to form sealed rectangular pockets 44 extending transversely of the bladder. The sealed pockets 44 remain uninflated despite inflation of the bladder 12. It is to be understood that a cushion may have greater or fewer than two flexible regions and still fall within the scope of the present invention. Because the sealed pockets 44 do not inflate despite inflation of the remaining portions of the bladder 12, they remain flexible and bend easily as the cushion 10 is wrapped around the leg L.

The flexible regions 38 also include passage means 48 for fluid communication between adjacent sections 36 of the bladder 12. The sealed pockets 44 do not extend the entire width of the bladder 12 and each of their longitudinal ends are spaced from a corresponding longitudinal edge of the bladder. This space between the ends of the sealed pockets 44 and corresponding adjacent edges of the bladder 12 defines the passage means 48 through the flexible regions 38. Thus, the entire bladder 12 may be inflated from a single air inlet means (tube 24) in one of the sections 36. Although the passage means 48 are inflated, they constitute only a small portion of the flexible region 38 and therefore do not, despite their inflation, add any appreciable rigidity to the flexible regions.

The lining 28 of synthetic lamb's wool provides a soft, comfortable surface for engagement of the leg L with the cushion L which prevents irritation and breakdown of the skin tissue contacting the cushion 10. Therefore, infection caused by breakdown of skin tissue is avoided. Moreover, the synthetic lamb's wool is a hypo-allergenic material which protects the skin from an allergic reaction despite extended contact with the lining 28. Growth of infectious bacteria on the skin is inhibited by the lining 28. Persons wearing the cushion 10 for extended periods will excrete body fluids (e.g., sweat) inside the cushion. The absorbent lining material draws away from the skin sweat and other body fluids which would otherwise promote bacteria growth on the skin leading to infection. The lining 28 may be made of other absorbent, hypo-allergenic material and still fall within the scope of the present invention. The lining 28 is releasably attached to the inner face 18 of the bladder by three straps 52 spaced longitudinally of the bladder 12 and by snap fasteners 53 close to the first and second ends 13, 14 of the bladder. The straps 52 extend transversely across the bladder 12 and are attached at their opposite ends to corresponding longitudinal edge margins of the bladder. The lining material is washable. Thus, the lining 28 may easily be removed, washed and reattached for repeated use over a long period of time.

To secure the cushion 10 to the leg, the bladder 12 is provided with a first flexible fastening flap 56 at the first end 13 of the bladder and a second flexible fastening flap 58 at the second end 14 of the bladder 12. The fastening means 16 preferably comprises a hook and loop type fastener (commonly referred to by the trademark VELCRO). The fastener includes first and second fastener elements indicated at 60 and 62, respectively. Each fastener element comprises a rectangular sheet of hook and loop material. The first fastener element 60 is carried by the first fastener flap 56 on the inner face 18 of the bladder (FIG. 2), and the second fastener element 62 is carried by the second fastener flap 58 on the outer face 20 of the bladder (FIG. 3). When the bladder 12 is wrapped around the leg, the first flap 56 overlaps the second flap 58 so that the fastening elements 60, 62 may be engaged to hold the cushion 10 around the leg. The fastening elements are elongate so that the diameter enclosed by the cushion 10 may be changed according to the size of the leg and to the desired tightness. The compartmentalization of the bladder 12 into three sections leaves gaps between the leg and bladder when the cushion 10 is wrapped around the leg. The adjustability of the cushion 10 and the provision of gaps helps to assure that the cushion will not cut off the flow of blood to the foot.

In view of the above, it will be seen that the several objects of the invention are achieved and other advantageous results attained. More specifically, it may be seen that the inflatable cushion 10 of the present invention supports the elevated extremity comfortably on a cushion of air. The inner face 18 of the inflated bladder 12 may resiliently deform under the weight of the extremity to support the weight of the extremity substantially uniformly over the area of the inner face of the bladder underlying the extremity, which prevents the occurrence of pressure points on the extremity. Pressure points cause pain, because the weight of the extremity is supported on only a small area of the extremity, as well as irritation and breakdown of the skin tissue. The flexible regions 38 of the bladder 12 and fastening means 16 allow the cushion 10 to be easily wrapped around the extremity and secured on the extremity so that although the person wearing the cushion may move around on the supporting surface S, elevation of the extremity is maintained. The ability to maintain elevation despite movement of the extremity provides a considerable advantage over elevating the extremity by propping it on a pillow or the like. The pillow, unlike the cushion 10, has no attachment to the extremity, and thus will not move with the extremity. Therefore, it is likely, as the persons moves to find a comfortable body position, that the extremity will occasionally fall from the pillow causing pain and annoyance. Further, the cushion 10 supports the extremity away from the bony protuberances, such as the heel, so that the weight of the extremity can be distributed uniformly over its area of contact with the cushion. The cushion 10 encircles the extremity so that as the extremity is turned a new portion of the outer face 20 of the bladder engages the surface S to maintain elevation of the extremity. The lining 28 made of synthetic lamb's wool which contacts the extremity is soft, absorbent and hypo-allergenic to prevent breakdown and infection of the skin. When not in use, the bladder 12 can be deflated and the cushion 10 folded into a compact configuration for storage. The cushion 10 of the preferred embodiment described herein weighs only 6.8 ounces when inflated with air and thus it comfortable to wear. The cushion 10 of the present invention is simply designed and made of inexpensive materials so that it is affordable for the average individual. Thus, persons such as diabetics suffering from chronic swelling may use the inflatable cushion of the present invention in their own home for reliable comfortable elevation of the swollen extremity.

As various changes could be made in the above constructions without departing from the scope of the invention, it is intended that all matter contained in the above description or shown in the accompanying drawings shall be interpreted as illustrative and not in a limiting sense.

What is claimed is:

1. An inflatable cushion for elevation of an extremity with respect to a surface supporting the cushion, the inflatable cushion comprising, an inflatable bladder having first and second opposite ends and inner and outer faces, inlet means for admitting air into the bladder for inflation thereof, means for selectively sealing and unsealing said inlet means, means for releasably fastening said first end of the bladder to said second end, lining means made of a soft absorbent material, means for releasably connecting said lining means to said inner face of the bladder such that the lining substantially covers said inner face of the bladder, the bladder being adapted to be inflated, wrapped around the extremity and secured by said fastening means such that the bladder completely encircles the extremity, said inner face of the bladder facing inwardly with said lining means disposed between the bladder and the extremity and engaging the extremity, an area of said inner face underlying the extremity resiliently deforming under the weight of the extremity such that the weight of the extremity is supported substantially uniformly over said underlying area of said inner face, and said outer face of the bladder facing outwardly with a portion of said outer face engaging the surface.

2. The inflatable cushion as set forth in claim 1 wherein said lining means is made of hypo-allergenic material.

3. The inflatable cushion as set forth in claim 1 wherein said connecting means comprises first and second connector members, said first connector members being affixed to said lining means and said second connector members being affixed to said inner face of the bladder, said first and second snap connector members being releasably interengageable for releasably connecting said lining means to said inner face of the bladder.

4. The inflatable cushion as set forth in claim 1 wherein said connecting means comprises strap means attached to the bladder, said lining means being adapted for insertion between said strap means and said inner face of the bladder for connecting said lining means to said bladder.

5. The inflatable cushion as set forth in claim 4 wherein said strap means comprises a plurality of straps attached to the bladder at locations spaced longitudinally of the bladder, each strap extending transversely of the bladder.

6. An inflatable cushion for elevation of an extremity with respect to a surface supporting the cushion, the inflatable cushion comprising, an inflatable bladder having first and second opposite ends and inner and outer faces, inlet means for admitting air into the bladder for inflation thereof, means for selectively sealing and unsealing said inlet means, means for releasably fastening said first end of the bladder to said second end, a lining comprising an elongate, rectangular piece of soft, absorbent, hypo-allergenic material, means for releasably connecting the lining to said inner face of the bladder such that the lining substantially covers said inner face of the bladder, said connecting means including first and second connector members, said first connector members being affixed to the lining and said second connector members being affixed to said inner face of the bladder, and a plurality of straps attached to the bladder at locations spaced longitudinally of the bladder, each strap extending transversely of the bladder, the lining being adapted for insertion between said straps and said inner face of the bladder and said first and second snap connector members being releasably interengageable thereby releasably connecting the lining to said inner face of the bladder, the bladder being adapted to be inflated, wrapped around the extremity and secured by said fastening means such that the bladder completely encircles the extremity, said inner face of the bladder facing inwardly with the lining disposed between the bladder and the extremity and engaging the extremity, an area of said inner face underlying the extremity resiliently deforming under the weight of the extremity such that the weight of the extremity is supported substantially uniformly over said underlying area of said inner face, and said outer face of the bladder facing outwardly with a portion of said outer face engaging the surface.

* * * * *